(12) United States Patent  
Amago et al.

(10) Patent No.: US 8,404,498 B2  
(45) Date of Patent: Mar. 26, 2013

(54) METHOD OF INSPECTING SEMICONDUCTOR THIN FILM BY TRANSMISSION IMAGING AND INSPECTION DEVICE FOR THE SAME

(75) Inventors: Hirohisa Amago, Kanagawa (JP); Nobuhiko Umezu, Kanagawa (JP)

(73) Assignee: Sony Corporation, Tokyo (JP)

( * ) Notice: Subject to any disclaimer, the term of this patent is extended or adjusted under 35 U.S.C. 154(b) by 425 days.

(21) Appl. No.: 12/537,299

(22) Filed: Aug. 7, 2009

(65) Prior Publication Data

US 2009/0298208 A1 Dec. 3, 2009

(30) Foreign Application Priority Data

Aug. 15, 2007 (JP) .................................. 2007-211734  
Aug. 14, 2008 (JP) .................................. 2008-208818

(51) Int. Cl.  
*G01R 31/26* (2006.01)

(52) U.S. Cl. ... 438/16; 438/166; 356/237.5; 257/E21.53

(58) Field of Classification Search .................... 438/16, 438/166; 356/237.5; 257/E21.53  
See application file for complete search history.

(56) References Cited

U.S. PATENT DOCUMENTS

| | | | |
|---|---|---|---|
| 5,298,977 A * | 3/1994 | Shintani et al. | 356/603 |
| 5,861,952 A * | 1/1999 | Tsuji et al. | 356/484 |
| 6,005,965 A * | 12/1999 | Tsuda et al. | 382/145 |
| 6,764,886 B2 * | 7/2004 | Yamazaki et al. | 438/164 |
| 6,781,687 B2 * | 8/2004 | Fisch et al. | 356/237.2 |
| 6,801,650 B1 * | 10/2004 | Kikuchi et al. | 382/145 |
| 6,977,775 B2 | 12/2005 | Sasaki et al. | |
| 7,184,132 B2 * | 2/2007 | Tsao | 356/30 |
| 7,446,864 B2 * | 11/2008 | Okabe et al. | 356/237.1 |
| 7,589,541 B2 * | 9/2009 | Yamasaki | 324/754.23 |
| 2002/0160586 A1 * | 10/2002 | Wada et al. | 438/509 |
| 2005/0002016 A1 * | 1/2005 | Tsao | 356/30 |
| 2005/0190361 A1 * | 9/2005 | Ishiba et al. | 356/237.2 |
| 2006/0072807 A1 * | 4/2006 | Bultman et al. | 382/149 |
| 2007/0072349 A1 * | 3/2007 | Kaitoh et al. | 438/149 |

FOREIGN PATENT DOCUMENTS

| | | |
|---|---|---|
| JP | 2003-332235 | 11/2003 |
| JP | 2004-153150 | 5/2004 |
| JP | 2004-342875 | 12/2004 |
| JP | 2005-101202 | 4/2005 |

* cited by examiner

*Primary Examiner* — David Vu  
*Assistant Examiner* — Caleb Henry  
(74) *Attorney, Agent, or Firm* — SNR Denton US LLP

(57) ABSTRACT

A method of forming a semiconductor thin film includes: a step of forming an amorphous semiconductor thin film over a transparent substrate; a step of forming a crystalline semiconductor thin film by irradiating the amorphous semiconductor thin film with laser light to provide heat treatment and thereby crystallizing the amorphous semiconductor thin film; and an inspection step of inspecting the crystalline semiconductor thin film. The inspection step includes a step of obtaining a transmission image of the crystalline semiconductor thin film by irradiating the crystalline semiconductor thin film with light from a rear side of the transparent substrate and taking an image, and a screening step of performing screening of the crystalline semiconductor thin film based on the obtained transmission image.

14 Claims, 9 Drawing Sheets

METHOD OF INSPECTING SEMICONDUCTOR THIN FILM BY TRANSMISSION IMAGING AND INSPECTION DEVICE FOR THE SAME

BACKGROUND OF THE INVENTION

1. Field of the Invention

The present invention relates to a method of forming a semiconductor thin film suitable for manufacturing a TFT (Thin Film Transistor) substrate used for a liquid crystal display or an organic EL (electroluminescence) display and an inspection device of such a semiconductor thin film.

2. Description of the Related Art

In an active matrix type liquid crystal display or an organic EL display using an organic EL device, a TFT substrate is used. In the TFT substrate, an amorphous semiconductor thin film or a polycrystalline semiconductor thin film with a relatively small grain diameter is formed on a substrate, and the semiconductor thin film is irradiated with a laser beam and annealed to obtain a crystal grown semiconductor thin film. The obtained semiconductor thin film is used to form a TFT as a drive element.

As a light source of an annealing device by a laser beam as above, in the past, excimer laser that has a high absorption rate of the semiconductor thin film and is capable of obtaining high pulsed light output has been used. However, since the excimer laser is gas laser, the output intensity varies according to every pulse. Thus, there is a disadvantage that in the TFT formed by using the excimer laser, the characteristics vary, and in a display unit using such a TFT, display irregularity is easily generated.

Therefore, for the purpose of resolving image quality deterioration due to the pulse intensity variation in gas laser, an annealing device using semiconductor laser with high output stability as a light source has been proposed (for example, Japanese Unexamined Patent Application Publication No. 2003-332235). However, since the light output obtained from the semiconductor laser is extremely small compared to that of the excimer laser or the like, the beam size in annealing treatment is also decreased. Therefore, annealing treatment time per unit area of the TFT substrate is increased, leading to disadvantages such as lowering of productivity and increase of manufacturing cost.

As a result, for the purpose of realizing a high throughput of annealing treatment, the following annealing method has been proposed (for example, Japanese Unexamined Patent Application Publication No. 2004-153150). In the annealing method, a plurality of laser light sources are arranged close to each other, and a plurality of regions on an amorphous semiconductor thin film are concurrently irradiated with a plurality of laser beams from the plurality of laser light sources. As a result, scanning time is reduced to increase productivity.

Meanwhile, in the past, a method of controlling crystallization of the semiconductor thin film using the semiconductor laser as above has been performed by a means for monitoring a laser beam intensity provided for the annealing device. For example, in the method of monitoring a laser beam intensity described in Japanese Unexamined Patent Application Publication No. 2005-101202, a single intensity measurement section is used for light paths of a plurality of laser optical systems. The single intensity measurement section is moved onto each light path of each laser optical system to allow the single intensity measurement section to receive light in each light path. Thereby, for the plurality of laser optical systems, each irradiation energy is measured by the single intensity measurement section.

Further, in Japanese Unexamined Patent Application Publication No. 2004-342875, a method of analyzing a laser irradiation position by using Raman scattering light emitted from crystal by irradiation of a laser beam is proposed. In addition, a defect inspection method and a device thereof using a reflection image of a high speed line camera have been proposed.

SUMMARY OF THE INVENTION

However, in the case where the annealing treatment is performed by using the plurality of laser beams as in the foregoing Japanese Unexamined Patent Application Publication No. 2005-101202, in the respective laser light sources, there is an individual difference between each divergence angle of each emitted light. Further, in the case where a uniform irradiation optical system is provided to correct such an individual difference, an adjustment error or the like occurs. Thus, in the case where the annealing treatment is performed by using the plurality of laser beams, it naturally results in a difference in size and intensity of each laser light with which a target is irradiated.

As described above, in the past, only the intensity (power) of a laser beam from each laser light source has been monitored. Thus, it is difficult to monitor a subtle power density difference on the target face due to a focus position, optical system aberration and the like. Therefore, such a power density difference leads to a difference of annealing effect on the target (semiconductor thin film), and further leads to a difference of crystallinity according to position on the semiconductor thin film. As a result, characteristics of the formed TFT differ according to each laser beam. The characteristic difference of the TFT causes a display irregularity in the display device.

Such a difference of laser annealing effect on the semiconductor thin film (difference of effect according to position on the thin film) may be generated not only in the case where annealing treatment is performed by using the plurality of laser light sources as above, but also in the case where annealing treatment is performed by using a single laser light source.

Meanwhile, in the technique in the foregoing Japanese Unexamined Patent Application Publication No. 2004-342875, since the Raman scattering light is used, the device scale becomes large and the cost becomes high. Further, since argon laser is used as a light source, the running cost is expensive. Further, since a complicated optical system is necessitated, labor and time are consumed for adjustment. Further, since the Raman light is faint, it is necessary to narrow laser light to the degree of about 1 μm, and a plurality of measurement points should be provided to evaluate average crystallinity. As a result, there is a disadvantage that time necessary for monitoring is increased.

Further, in the foregoing defect inspection method by using the reflection image of the high speed line camera, since the reflection image is used, many noises referred to as false defect are included. Thus, it is often the case that a person should check the authenticity of a prospective defect, leading to a disadvantage in respect of measurement time and measurement precision.

In view of the foregoing, in the invention, it is desirable to provide a method of forming a semiconductor thin film capable of precisely and easily evaluating a crystalline semiconductor thin film in forming a semiconductor thin film with the use of crystallization by laser annealing and an inspection device of a semiconductor thin film.

According to an embodiment of the invention, there is provided a method of forming a semiconductor thin film including: a step of forming an amorphous semiconductor thin film over a transparent substrate; a step of forming a crystalline semiconductor thin film by irradiating the amorphous semiconductor thin film with laser light to provide heat treatment and thereby crystallizing the amorphous semiconductor thin film; and an inspection step of inspecting the crystalline semiconductor thin film. The inspection step includes a step of obtaining a transmission image of the crystalline semiconductor thin film by irradiating the crystalline semiconductor thin film with light from a rear side of the transparent substrate and taking an image, and a screening step of performing screening of the crystalline semiconductor thin film based on the obtained transmission image.

In the method of forming a semiconductor thin film of the embodiment of the invention, after the amorphous semiconductor thin film is formed over the transparent substrate, the amorphous semiconductor thin film is irradiated with laser light to provide heat treatment. Thereby, the amorphous semiconductor thin film is crystallized, and the crystalline semiconductor thin film is formed. After that, the inspection of the crystalline semiconductor thin film is performed. In the inspection step, the transmission image of the crystalline semiconductor thin film is obtained by irradiating the crystalline semiconductor thin film with light from the rear face side of the transparent substrate and taking an image, and screening of the crystalline semiconductor thin film is performed based on the transmission image.

According to an embodiment of the invention, there is provided an inspection device of a semiconductor thin film, including: a stage mounting a transparent substrate over which a crystalline semiconductor thin film is formed in inspecting the crystalline semiconductor thin film that has been crystallized and formed by forming an amorphous semiconductor thin film over the transparent substrate, and then irradiating the amorphous semiconductor thin film with laser light to provide heat treatment; a light source irradiating the crystalline semiconductor thin film with light from a rear side of the stage; an image pickup means for receiving transmitted light that has been emitted from the light source and transmitted through the stage and the crystalline semiconductor thin film, and thereby obtaining a transmission image of the crystalline semiconductor thin film; and a screening means for performing screening of the crystalline semiconductor thin film based on the transmission image obtained by the image pickup means.

In the inspection device of a semiconductor thin film of the embodiment of the invention, the light source irradiates the crystalline semiconductor thin film with light from the rear side of the stage mounting the transparent substrate over which the crystalline semiconductor thin film is formed, and the transmitted light that has been transmitted through the stage and the crystalline semiconductor thin film is received. Thereby, the transmission image of the crystalline semiconductor thin film is obtained. Based on the transmission image, screening of the crystalline semiconductor thin film is performed.

According to the method of forming a semiconductor thin film of the embodiment of the invention, in the step of inspecting the crystallinity of the crystalline semiconductor thin film, the transmission image of the crystalline semiconductor thin film is obtained by irradiating the crystalline semiconductor thin film with light from the rear face side of the transparent substrate and taking an image, and screening of the crystalline semiconductor thin film is performed based on the transmission image. Therefore, in forming the semiconductor thin film by using crystallization with the use of laser annealing, evaluation of the crystalline semiconductor thin film is precisely and easily performed.

Further, according to the inspection device of a semiconductor thin film of the embodiment of the invention, the light source irradiates the crystalline semiconductor thin film with light from the rear side of the stage mounting the transparent substrate over which the crystalline semiconductor thin film is formed, the transmitted light that has been transmitted through the stage and the crystalline semiconductor thin film is received, and thereby the transmission image of the crystalline semiconductor thin film is obtained. In addition, based on the transmission image, screening of the crystalline semiconductor thin film is performed. Therefore, in forming the semiconductor thin film by using crystallization with the use of laser annealing, evaluation of the crystalline semiconductor thin film is precisely and easily performed.

Other and further objects, features and advantages of the invention will appear more fully from the following description.

DETAILED DESCRIPTION OF THE PREFERRED EMBODIMENT

An embodiment of the invention will be hereinafter described in detail with reference to the drawings.

Figure 1:
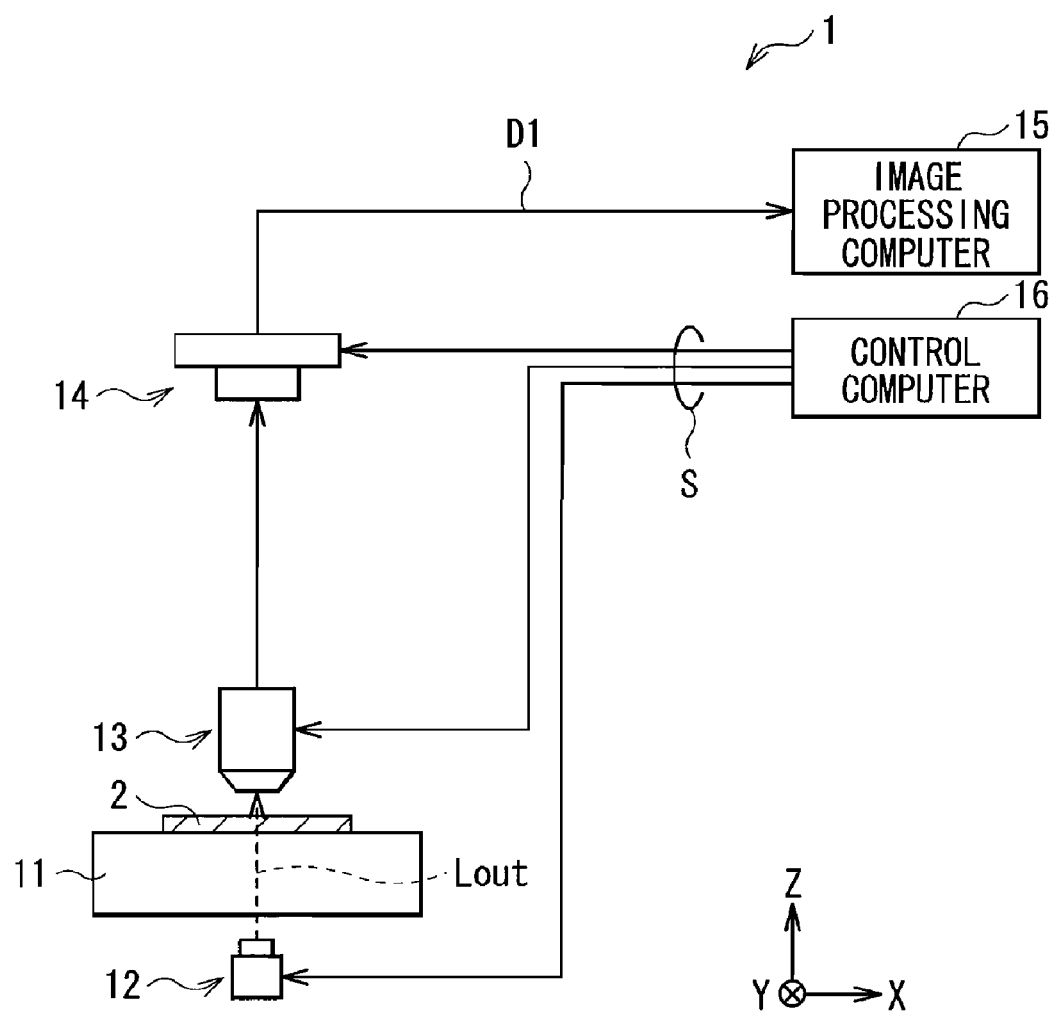
FIG. 1 is a view illustrating a whole configuration of an inspection device of a semiconductor thin film according to an embodiment of the invention.

FIG. 1 illustrates a whole configuration of an inspection device of a semiconductor thin film (inspection device 1) according to an embodiment of the invention. The inspection device 1 is applied to, for example, a silicon semiconductor film formed in a step of manufacturing a thin film transistor (bottom gate type TFT) having a bottom gate structure. Specifically, the inspection device 1 is an inspection device of crystallinity applied to a Si (silicon) thin film substrate 2 (as will be described later, a substrate having a p-Si (polysilicon) film (crystalline semiconductor thin film) that is crystallized and formed by forming an a-Si (amorphous silicon) film (amorphous semiconductor thin film) over a transparent substrate, and then irradiating the a-Si film with laser light to provide annealing treatment). The inspection device 1 includes a movable stage 11, an LED (Light Emitting Diode) 12, an objective lens 13, a CCD (Charge Coupled Device) camera 14, an image processing computer 15, and a control computer 16.

The movable stage 11 mounts (supports) the Si thin film substrate 2 as an inspection target. The movable stage 11 is able to be voluntarily moved in an X-axis direction and a Y-axis direction in the drawing by a control signal S supplied from the after-mentioned control computer 16. Further, the movable stage 11 is made of a material (for example, a glass plate) through which light generated from the after-mentioned LED 12 (irradiated light $L_{out}$) is able to be transmitted.

The LED 12 is a light source that irradiates the Si thin film substrate 2 with light (irradiated light $L_{out}$) from the rear side of the movable stage 11 (on the other side of the face on which the Si thin film substrate 2 is mounted). The LED 12 preferably irradiates the Si thin film substrate 2 with green light that is light in a wavelength range having a central wavelength of about from 500 to 600 nm both inclusive as the irradiated light $L_{out}$. The green light is light in the wavelength range that is easily transmitted through the p-Si thin film as an irradiation target.

The objective lens 13 is an optical device for magnifying and detecting the irradiated light $L_{out}$ (transmitted light) that is emitted from the LED 12 and is transmitted through the movable stage 11 and the Si thin film substrate 2. The CCD camera 14 is a camera that is highly sensitive to the light in the wavelength range of about from 500 to 600 nm both inclusive. The CCD camera 14 therein has a CCD image sensor as an image pickup device, and thereby takes a transmission microscope image (transmission image) of the p-Si thin film in the Si thin film substrate 2.

The image processing computer 15 generates a luminance distribution described later based on the transmission image of the p-Si film obtained by the objective lens 13 and the CCD camera 14, and performs screening of the p-Si film (perform inspection processing) by using the generated luminance distribution. Specifically, first, the image processing computer 15 takes in transmission image data D1 supplied from the CCD camera 14, analyzes the image luminance, and monitors the crystallization state (crystallinity) of the p-Si film formed over the Si thin film substrate 2. Based on the monitoring result, the image processing computer 15 obtains a set value of an energy density in semiconductor laser annealing for generating the p-Si film, or determines whether the p-Si film formed over the Si thin film substrate 2 is a non-defective product or a defective product. For details of the inspection processing by the image processing computer 15 will be described later.

The control computer 16 controls lighting of the irradiated light $L_{out}$ from the LED 12, controls movement position of the LED 12, the objective lens 13, and the CCD camera 14, and controls switching of the objective lens 13 based on the control signal S. Of the foregoing, for controlling movement position, specifically, the control computer 16 performs control so that the positions of the LED 12, the objective lens 13, and the CCD camera 14 are relatively changed with respect to the Si thin film substrate 2 mounted on the movable stage 11.

In this embodiment, the LED 12 corresponds to a specific example of "light source" in the invention. Further, the objective lens 13 and the CCD camera 14 correspond to a specific example of "image pickup means" in the invention. Further, the image processing computer 15 corresponds to a specific example of "luminance distribution generation means" and "screening means" in the invention. Further, the control computer 16 corresponds to a specific example of "control means" in the invention.

Figure 2:
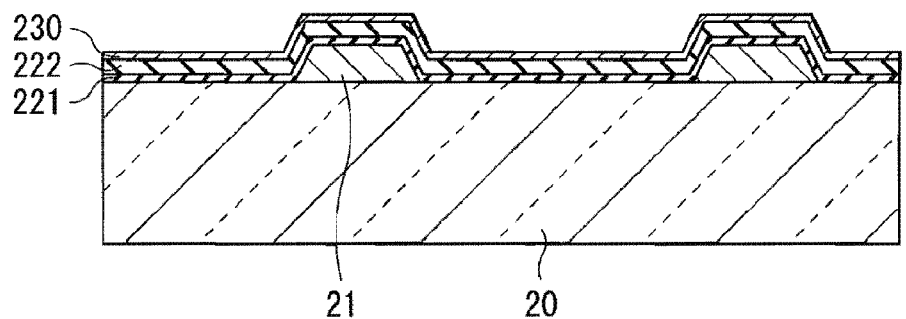
FIG. 2 is a cross sectional view illustrating part of main steps of forming a semiconductor thin film according to an embodiment of the invention.
Figure 3:
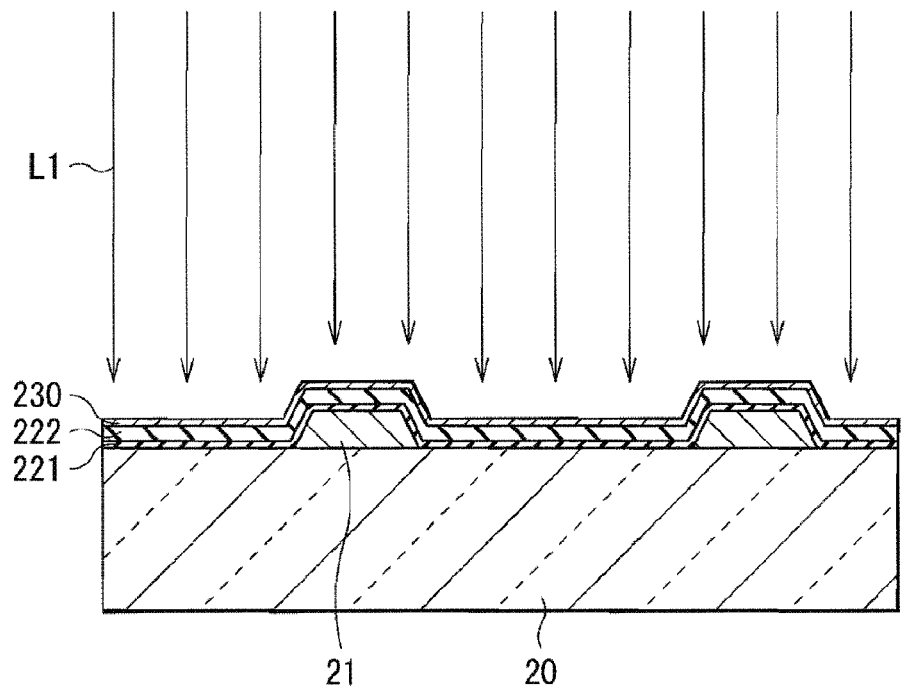
FIG. 3 is a cross sectional view illustrating a step following FIG. 2.
Figure 4:
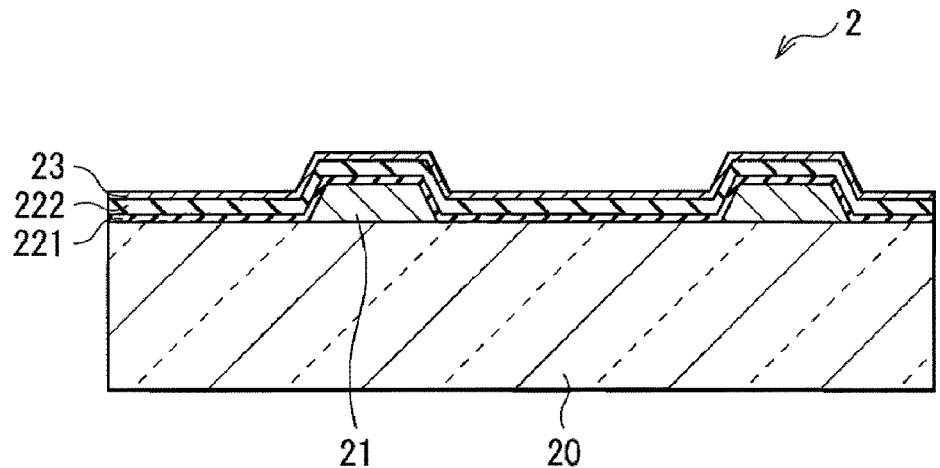
FIG. 4 is a cross sectional view illustrating a step following FIG. 3.
Figure 5:
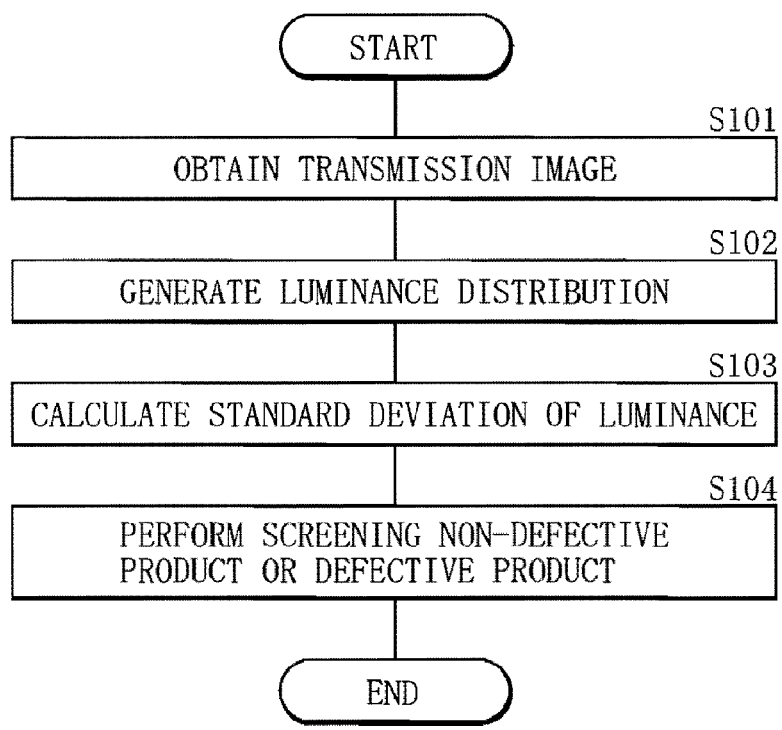
FIG. 5 is a flowchart illustrating an example of a step (inspection step) following FIG. 4.

Next, a description will be given of a method of forming a semiconductor thin film according to an embodiment of the invention that includes an inspection step using the inspection device 1 illustrated in FIG. 1 with reference to FIG. 2 to FIG. 7B. FIG. 2 to FIG. 4 are cross sectional views illustrating part of main steps of the method of forming a semiconductor thin film according to this embodiment. FIG. 5 is a flowchart illustrating an example of a step (inspection step) following FIG. 4.

First, as illustrated in FIG. 2, on a transparent substrate 20 such as a glass substrate (the substrate size is, for example, about 550 mm×650 mm), for example, by using photolithography method, a gate electrode 21, a gate insulating films 221 and 222, and an a-Si film 230 are formed in this order. The gate electrode 21 is composed of, for example, molybdenum (Mo), and the gate insulating film 221 is composed of, for example, silicon nitride (SiNx), and the gate insulating film 222 is composed of, for example, silicon oxide ($SiO_2$).

Next, as illustrated in FIG. 3, the a-Si film 230 over the transparent substrate 20 is irradiated with laser light L1 by using a semiconductor laser light source (not illustrated) to provide annealing treatment (heat treatment), and thereby the a-Si film 230 is crystallized. Thereby, for example, as illustrated in FIG. 4, the p-Si film 23 is formed over the transparent substrate 20. Irradiation condition in providing such an annealing treatment is, for example, 15 $J/cm^2$.

Next, for example, as illustrated in steps S101 to S104 in FIG. 5, by using the inspection device 1 illustrated in FIG. 1, the crystallization state (crystallinity) of the p-Si film 23 formed over the transparent substrate 20 is inspected (inspection processing is executed).

Figure 6A:
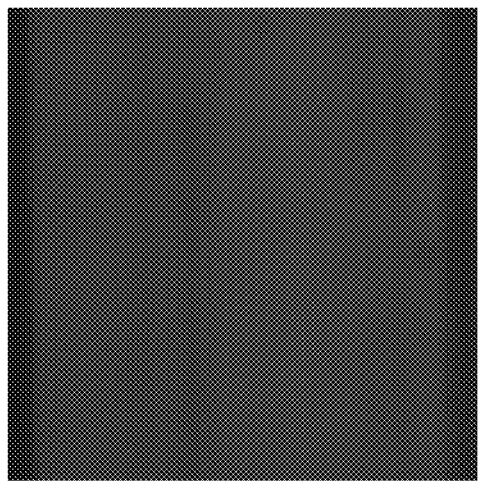
FIGS. 6A to 6C are photographs illustrating an example of transmission images of the semiconductor thin film obtained in the inspection step illustrated in FIG. 5.
Figure 6B:
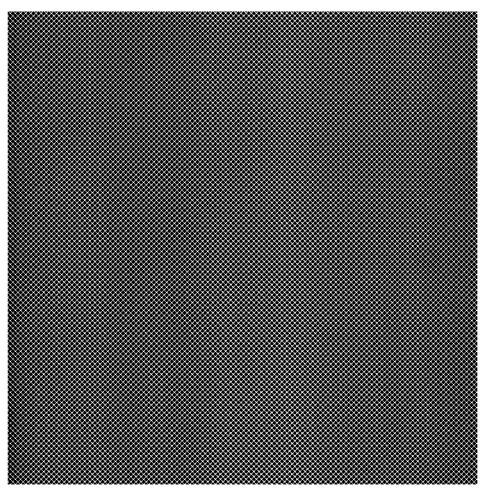
Figure 6C:
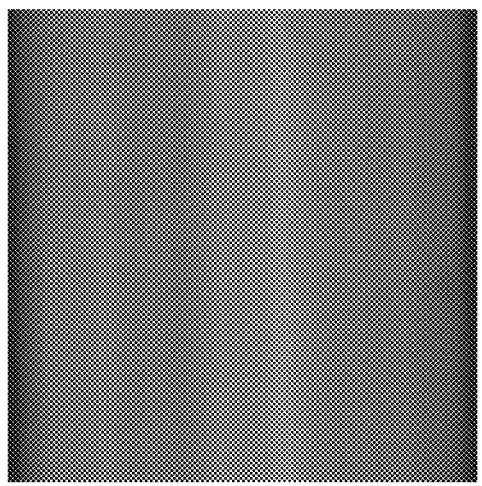

Specifically, first, the Si thin film substrate 2 over which the p-Si film 23 is formed is mounted on the movable stage 11, and the LED 12 irradiates the p-Si film 23 with the irradiated light $L_{out}$ from the rear side of the movable stage 11 (on the other side of the face on which the Si thin film substrate 2 is mounted). The objective lens 13 and the CCD camera 14 receive the transmitted light that has been transmitted through the movable stage 11 and the Si thin film substrate 2, and take an image. Thereby, in the image processing computer 15, a transmission image of the p-Si film 23 (transmission image data D1) as illustrated in FIGS. 6A to 6C is obtained (step S101 in FIG. 5). At this time, it is possible that the positions of the LED 12, the objective lens 13, and the CCD camera 14 are relatively changed with respect to the Si thin film substrate 2 mounted on the movable stage 11 by the control signal S supplied from the control computer 16, and thereby transmission images at a plurality of points on the p-Si film 23 are obtainable.

FIG. 6A illustrates an example of transmission images in the case of irradiation with the laser light L1 having a smaller energy density than an energy density necessary for crystallization of the whole irradiated face in annealing treatment by using the laser light L1. FIG. 6B illustrates an example of transmission images in the case of irradiation with the laser light L1 having the energy density necessary for crystallization of the whole irradiated face in annealing treatment by using the laser light L1. FIG. 6C illustrates an example of transmission images in the case of irradiation with the laser light L1 having a larger energy density than the energy density necessary for crystallization of the whole irradiated face in annealing treatment by using the laser light L1. From the transmission images of FIG. 6A to FIG. 6C, it is found that the image luminance in the transmission image of FIG. 6B is almost uniformized, while the image luminance in the transmission images of FIG. 6A and FIG. 6C is not uniformized. It results from the following reason. That is, since crystallinity of the Si film largely depends on the energy density in annealing treatment, and the transmittance of the Si film is increased as the crystallization region is enlarged or the crystal size is increased. Specifically, crystallization is progressed in only part of the irradiation region until a certain energy density, crystallization is realized in the whole irradiation region at such a certain energy density, and the crystal size is partially increased in part of the irradiation region as the energy density is further increased.

Figure 7A:
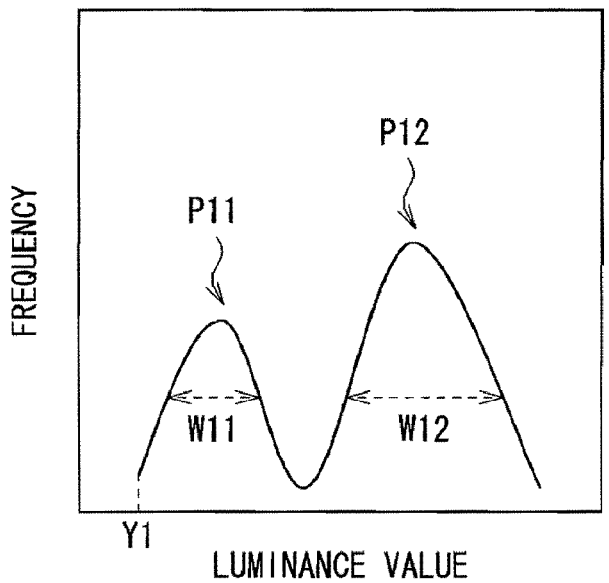
FIGS. 7A and 7B are characteristic diagrams illustrating an example of luminance distributions generated in the inspection step illustrated in FIG. 5.
Figure 7B:
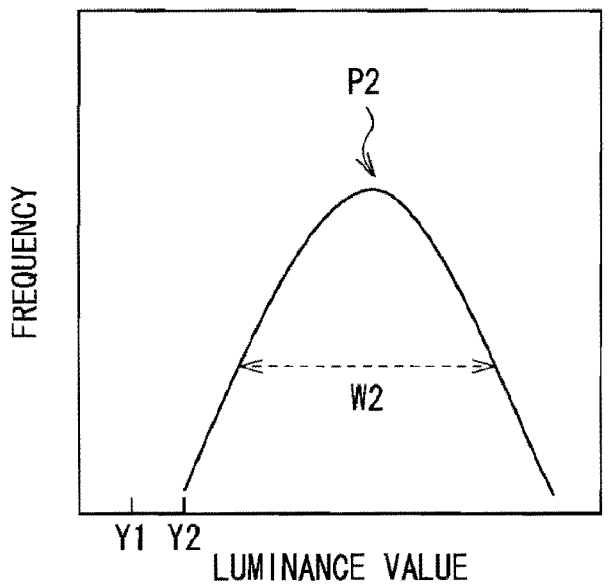

Next, for example, a luminance distribution of the transmission image (distribution indicating a relation between a luminance value and frequency of each luminance value) as illustrated in FIGS. 7A and 7B is generated based on the obtained transmission image (transmission image data D1) by the image processing computer 15 (step S102). FIG. 7A illustrates an example of luminance distributions corresponding to the case in which the image luminance of the transmission image is not uniformized as illustrated, for example, in FIGS. 6A and 6C. FIG. 7B illustrates an example of luminance distributions corresponding to the case in which the image luminance of the transmission image is almost uniformized as illustrated, for example, in FIG. 6B. From the luminance distributions of FIGS. 7A and 7B, it is found that in the case where the energy density in annealing treatment is smaller or unduly larger than the necessary energy density and thus the image luminance of the transmission image is not uniformized (FIGS. 6A and 6C), a plurality of (in this case, two) luminance peaks are generated. Meanwhile, it is found that in the case where the energy density in annealing treatment is almost the necessary energy density, and the image luminance of the transmission image is almost uniformized (FIG. 6B), a single luminance peak is generated.

Next, a standard deviation of the luminance is calculated based on the generated luminance distribution of the transmission image by the image processing computer 15 (step S103). Specifically, the image processing computer 15 performs calculation so that the standard deviation of the luminance is, for example, 7.9 in the luminance distribution of the transmission image illustrated in the foregoing FIG. 6A, the standard deviation of the luminance is, for example, 2.6 in the luminance distribution of the transmission image illustrated in the foregoing FIG. 6B, and the standard deviation of the luminance is, for example, 4.9 in the luminance distribution of the transmission image illustrated in the foregoing FIG. 6C.

Next, the image processing computer 15 performs screening of the p-Si film 23 according to the calculated standard deviation of luminance (performs screening whether the p-Si film 23 is a non-defective product or a defective product) (step S104). Specifically, in the case where the calculated standard deviation is under a given threshold value (for example, 3.5) (for example, the standard deviation calculated based on the luminance distribution of the transmission image of FIG. 6B is 2.6), the image processing computer 15 determines that the crystallinity of the p-Si film 23 is almost uniformized and the p-Si film 23 is a non-defective product. Meanwhile, in the case where the calculated standard deviation is the given threshold value (for example, 3.5) or more (for example, the standard deviations calculated based on the luminance distributions of the transmission images of FIGS. 6A and 6C are 7.9 and 4.9, respectively), the image processing computer 15 determines that the crystallinity of the p-Si film 23 is not uniformized and the p-Si film 23 is a defective product. Thereby, the inspection processing of the crystallinity of the p-Si film 23 formed over the transparent substrate 20 is finished.

As described above, in this embodiment, after the a-Si film 230 is formed over the transparent substrate 20, the a-Si film 230 is irradiated with the laser light L1 to provide annealing treatment (heat treatment). Thereby, the a-Si film 230 is crystallized, and the p-Si film 23 is formed. After that, the crystallinity of the p-Si film 23 is inspected by the inspection device 1 (inspection processing is performed). In the inspection processing, the LED 12 irradiates the p-Si film 23 with the irradiated light $L_{out}$ from the rear side of the movable stage 11 mounting the transparent substrate 20 (Si thin film substrate 2) on which the p-Si film 23 is formed. The transmitted light that has been transmitted through the movable stage 11 and the p-Si film 23 is received by the CCD camera 14 through the objective lens 13, and thereby the transmission image of the p-Si film 23 (transmission image data D1) is obtained. In the image processing computer 15 obtaining the transmission image data D1, the luminance distribution is formed based on the transmission image data D1, and screening of the p-Si film 23 is performed by using the luminance distribution.

As described above, in this embodiment in the inspection processing of crystallinity of the p-Si film 23, the LED 12 irradiates the p-Si film 23 with the irradiated light $L_{out}$ from the rear side of the movable stage 11 mounting the transparent substrate 20 (Si thin film substrate 2) on which the p-Si film 23 is formed. The transmitted light that has been transmitted through the movable stage 11 and the p-Si film 23 is received by the CCD camera 14 through the objective lens 13, and thereby the transmission image of the p-Si film 23 (transmission image data D1) is obtained. In the image processing computer 15, the luminance distribution is formed based on the transmission image data D1, and screening of the p-Si film 23 is performed by using the luminance distribution. Therefore, in forming the Si thin film with the use of the crystallization by laser annealing, the crystallinity is able to be precisely evaluated. Accordingly, even if a power density difference or the like on the target (a-Si film 230) resulting from a subtle focus position difference, a subtle laser beam diameter difference due to a divergence angle difference, a subtle optical system aberration and the like is generated, crystallization control by the semiconductor laser in annealing treatment is enabled. Further a difference of characteristics such as crystal grain size among each irradiation region on the p-Si film 23 is able to be decreased. Further, since crystallinity inspection is able to be performed for the Si thin film substrate 2 in a noncontact and nondestructive manner, crystallization monitoring with high reproducibility is able to be performed in a short time.

Specifically, in screening of the p-Si film 23, the standard deviation of luminance is calculated based on the generated luminance distribution, and screening is performed according to the standard deviation size. Thus, the foregoing effect is obtainable.

Further, in the case where the standard deviation is under a given threshold value, the image processing computer 15 determines that that the p-Si film 23 is a non-defective product (for example, FIG. 6B and FIG. 7B). Meanwhile, in the case where the standard deviation is the given threshold value or more, the image processing computer 15 determines that the p-Si film 23 is a defective product (for example, FIG. 6A, FIG. 6C, and FIG. 7A). Thus, simple screening is enabled.

Further, in obtaining the transmission image (transmission image data D1) of the p-Si film 23, as the irradiated light for the p-Si film 23 (irradiated light $L_{out}$), the light in the green wavelength range is used. Thus, in the p-Si thin film 23 as an irradiation target, the irradiated light $L_{out}$ is easily transmitted. Thus, it is possible that the image quality of the transmission image is improved, and more accurate screening is performed.

Further, in annealing treatment, in the case where irradiation with the laser light L1 is performed by using a plurality of laser light sources, it is possible that a throughput of annealing treatment is improved to perform annealing treatment in a short time. Further, even in the case of using the plurality of laser light sources as above, by performing the foregoing inspection processing, influence of intensity variation of laser light is able to be prevented, and in-plane variation of the characteristics of the p-Si film 23 is able to be decreased.

Further, the positions of the LED 12, the objective lens 13, and the CCD camera 14 are relatively changed with respect to the Si thin film substrate 2 mounted on the movable stage 11 by the control signal S supplied from the control computer 16, and thereby transmission images at a plurality of points on the p-Si film 23 are obtainable, and inspection at such a plurality of points is enabled.

While the invention has been described with reference to the embodiment, the invention is not limited to the foregoing embodiment, and various modifications may be made.

For example, in the foregoing embodiment, the description has been given of the case that in screening the p-Si film 23, the standard deviation of luminance is calculated based on the luminance distribution, and screening is performed according to the standard deviation. However, for example, it is possible that in screening the p-Si film 23, a peak width (for example, half bandwidths W11, W12, and W2 in FIGS. 7A and 7B) of a luminance peak (for example, luminance peaks P11, P12, and P2 in FIGS. 7A and 7B) is calculated based on the luminance distribution, and screening is performed according to the peak width. Specifically, in the case where the peak width is larger than a given threshold value, determination is made that the p-Si film 23 is a non-defective product (for example, FIG. 7B). Meanwhile, in the case where the peak width is the given threshold value or less, determination is made that the p-Si film 23 is a defective product (for example, FIG. 7A).

Further, similarly, for example, in screening of the p-Si film 23, it is possible that the minimum value of luminance (for example, minimum values Y1 and Y2 in FIGS. 7A and 7B) is calculated based on the luminance distribution, and the screening is performed according to the minimum value. Specifically, in the case where the minimum value is larger than a given threshold value, determination is made that the p-Si film 23 is a non-defective product (for example, FIG. 7B). Meanwhile, in the case where the minimum value is the given threshold value or less, determination is made that the p-Si film 23 is a defective product (for example, FIG. 7A).

Further, in screening the p-Si film 23, it is possible that screening is performed by using a luminance contrast value between a region of the a-Si film 230 irradiated with the laser light L1 and a region of the a-Si film 230 not irradiated with the laser light L1 in annealing treatment instead of using the standard deviation of luminance, the peak width of luminance peak, and the minimum value of luminance.

Figure 8A:
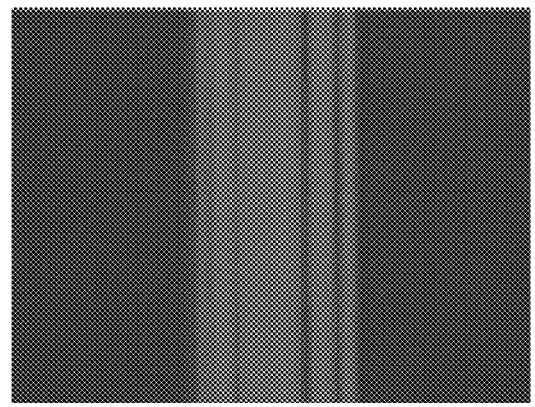
FIGS. 8A to 8C are photographs illustrating another example of transmission images of the semiconductor thin film obtained in the inspection step.
Figure 8B:
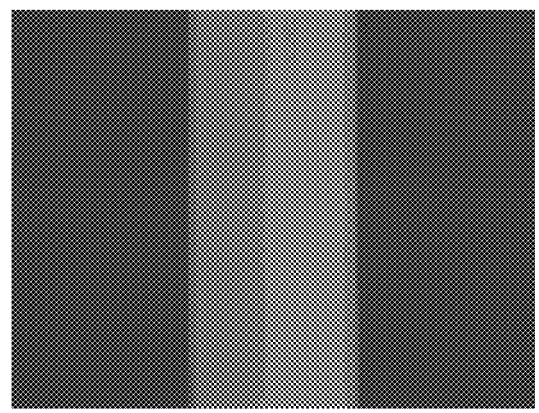
Figure 8C:
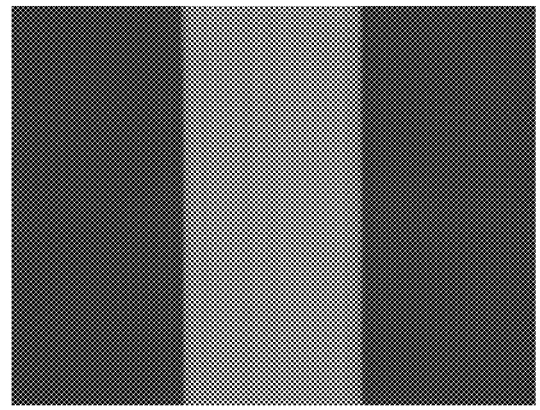
Figure 9:
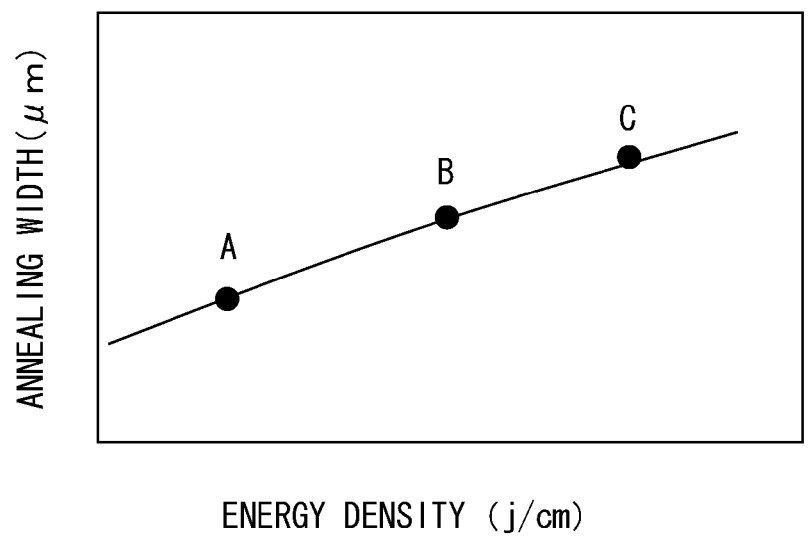
FIG. 9 is a characteristic diagram illustrating an example of a relation between an energy density and an annealing width.
Figure 10:
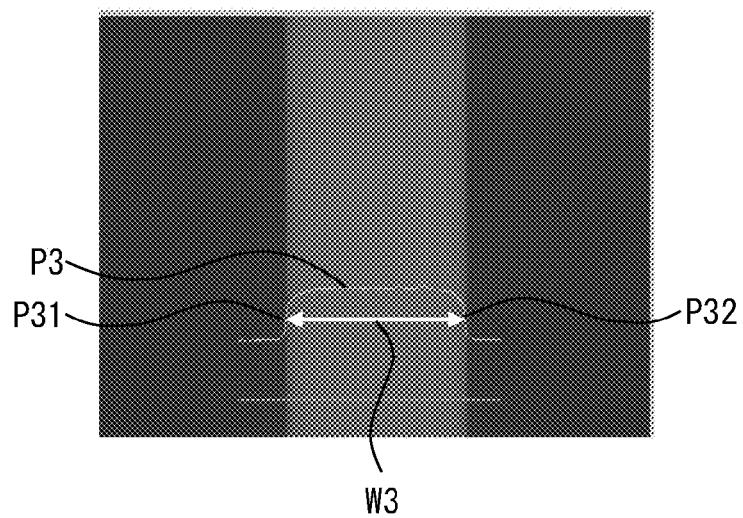
FIG. 10 is a photograph illustrating another example of transmission images of the semiconductor thin film obtained in the inspection step.

Further, in the foregoing embodiment, the description has been given of the case that in the inspection processing in the inspection device 1, crystallinity inspection of the p-Si film 23 formed over the transparent substrate 20 is performed. However, the inspection step and the inspection device of the invention are not limited thereto. Specifically, for example, it is possible that a width of a crystallized region (annealing region) is obtained based on the obtained transmission image, and the crystallization state of the p-Si film 23 is inspected according to the width of the crystallized region. FIG. 8A illustrates an example of transmission images in the case of irradiation with the laser light L1 having a smaller energy density than an energy density necessary for crystallization of the whole irradiated face in annealing treatment by using the laser light L1. FIG. 8B illustrates an example of transmission images in the case of irradiation with the laser light L1 having the energy density necessary for crystallization of the whole irradiated face in annealing treatment by using the laser light L1. FIG. 8C illustrates an example of transmission images in the case of irradiation with the laser light L1 having a larger energy density than the energy density necessary for crystallization of the whole irradiated face in annealing treatment by using the laser light L1. FIG. 9 illustrates an example of a relation between an energy density of the laser light L1 and a width of a portion having a high transmittance in each transmission image, that is, a width of a crystallized region (annealing width). Based on FIGS. 8A to 9, it is found that as the energy density in irradiation with the laser light L1 is increased, the width of the crystallized region is gradually increased. Therefore, it is possible that by using such characteristics, the obtained transmission image is provided with image processing to obtain the width of the crystallized region (annealing region), and the crystallization state of the p-Si film 23 is inspected according to the width of the crystallized region. FIG. 10 illustrates an example of numeric techniques of the width of the crystallized region based on the transmission image. In the transmission image illustrated in FIG. 10, a profile of the luminance average value along a direction perpendicular to the annealing direction is referred to as profile P3. In this case, point P31 at which luminance change is rapidly increased and point P32 at which luminance change is rapidly decreased are obtained from the luminance change value in the direction perpendicular to the annealing direction, a length of the line segment obtained by connecting the two points P31 and 32 is defined as a width W3 of the crystallized region (annealing region), and the value thereof is evaluated.

Figure 11:
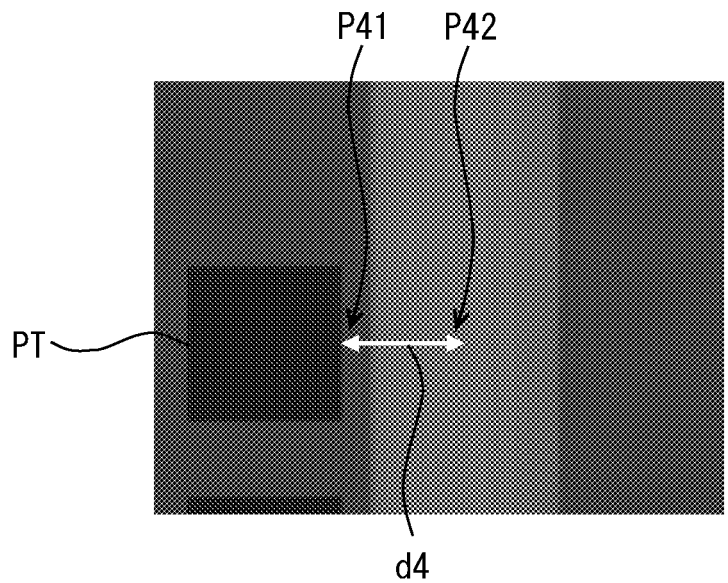
FIG. 11 is a photograph illustrating another example of transmission images of the semiconductor thin film obtained in the inspection step.

Further, for example, it is possible that a distance between a previously set given reference pattern and the crystallized region and a direction thereof are respectively obtained based on the obtained transmission image, and the crystallization position of the p-Si film 23 is inspected based on the distance and the direction. Specifically, for example, as illustrated in FIG. 11, a previously set reference pattern PT is detected in the transmission image, and a length of a line segment obtained by connecting central point P41 of a line in parallel with the annealing direction in the reference pattern PT and midpoint P42 of the annealing width obtained by, for example, the foregoing technique is obtained as a distance d4 between the reference pattern PT and the crystallized region and a direction thereof. The distance d4 and the direction are defined as a crystallization position (annealing position), and the value thereof is evaluated.

Figure 12:
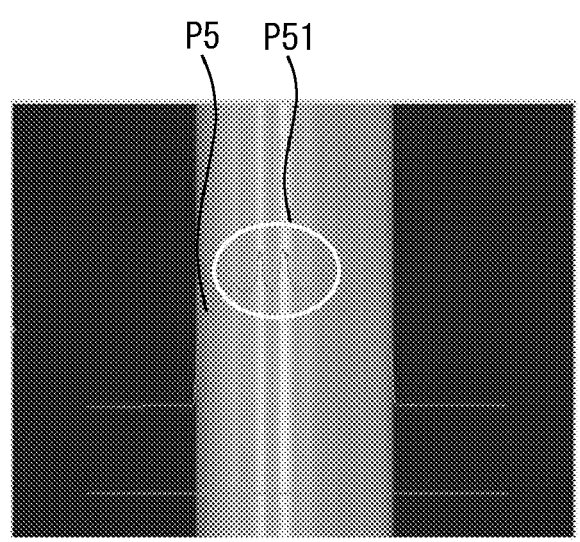
FIG. 12 is a photograph illustrating still another example of transmission images of the semiconductor thin film obtained in the inspection step.

Further, for example, it is possible that a spatial luminance distribution is obtained based on the obtained transmission image, and a physical destruction part in the p-Si film 23 (physical destruction part resulting from partially excessive energy density or the like in annealing) is inspected based on the spatial luminance distribution. Specifically, for example, as illustrated in FIG. 12, in the case where a profile of the luminance average value along a direction perpendicular to the annealing direction in the transmission image is referred to as profile P5, in the location where a physical destruction part due to annealing exists, a peak waveform largely exceeding the average luminance in the annealing width (for example, a portion indicated by symbol P51) appears. Thus, presence of such a peak waveform and the position thereof are evaluated.

As described above, in the inspection device 1 described in the foregoing embodiment, in addition to the crystallinity of the p-Si film 23, crystallization state, crystallization position, and a physical destruction part of the p-Si film 23 are able to be inspected. Specifically, the image processing computer 15 obtains the spatial image luminance distribution from the transmission image data (transmission image) of the p-Si film 23, and performs image processing from the value thereof. Thereby, high luminance width measurement of the p-Si film 23 (annealing width), the distance between the reference pattern PT and the central position of the high luminance width (crystallized region) (annealing position), presence of abnormal luminance peak in the high luminance width (physical destruction part) and the like are evaluated. Thereby, the crystallization state, the crystallization position, and the physical destruction part of the p-Si film 23 are inspected. For example, the annealing width is obtained, for example, as 187 μm in the transmission image illustrated in FIG. 8A described above, the annealing width is obtained, for example, as 196 μm in the transmission image illustrated in FIG. 8B described above, and the annealing width is obtained, for example, as 208 μm in the transmission image illustrated in FIG. 8C described above. In this case, the image of FIG. 8B is an image with the annealing width close to the control set value. Meanwhile, the image of FIG. 8A is an image with the annealing width smaller than the control set value, and FIG. 8C is an image with the annealing width larger than the control set value. Accordingly, it is possible that the annealing width is obtained based on the pickup image, and the crystal state of the p-Si film 23 is expressed as a numerical value. Further, the annealing position and the physical destruction part may be monitored similarly. As a result, the p-Si film 23 may be precisely and easily evaluated. Further, defect caused by irradiation displacement may be decreased, and abnormality of the annealing device may be detected, and high density of circuit design rule may be realized.

Further, in the foregoing embodiment, the description has been given of the case that in obtaining the transmission image of the p-Si film 23 (transmission image data D1), as the irradiated light $L_{out}$ for the p-Si film 23, the light in the green wavelength range is used. However, the wavelength range of the irradiated light $L_{out}$ is not limited thereto. An image pickup means in obtaining the transmission image is not limited to the objective lens 13 and the CCD camera 14 described in the foregoing embodiment, and may be other optical system.

Further, in the foregoing embodiment, the description has been given of the case that in forming the p-Si film 23 (in annealing treatment), irradiation with the laser light L1 is performed by using the semiconductor laser light source. However, other type of laser light source, for example, gas laser such as excimer laser may be used.

Figure 13:
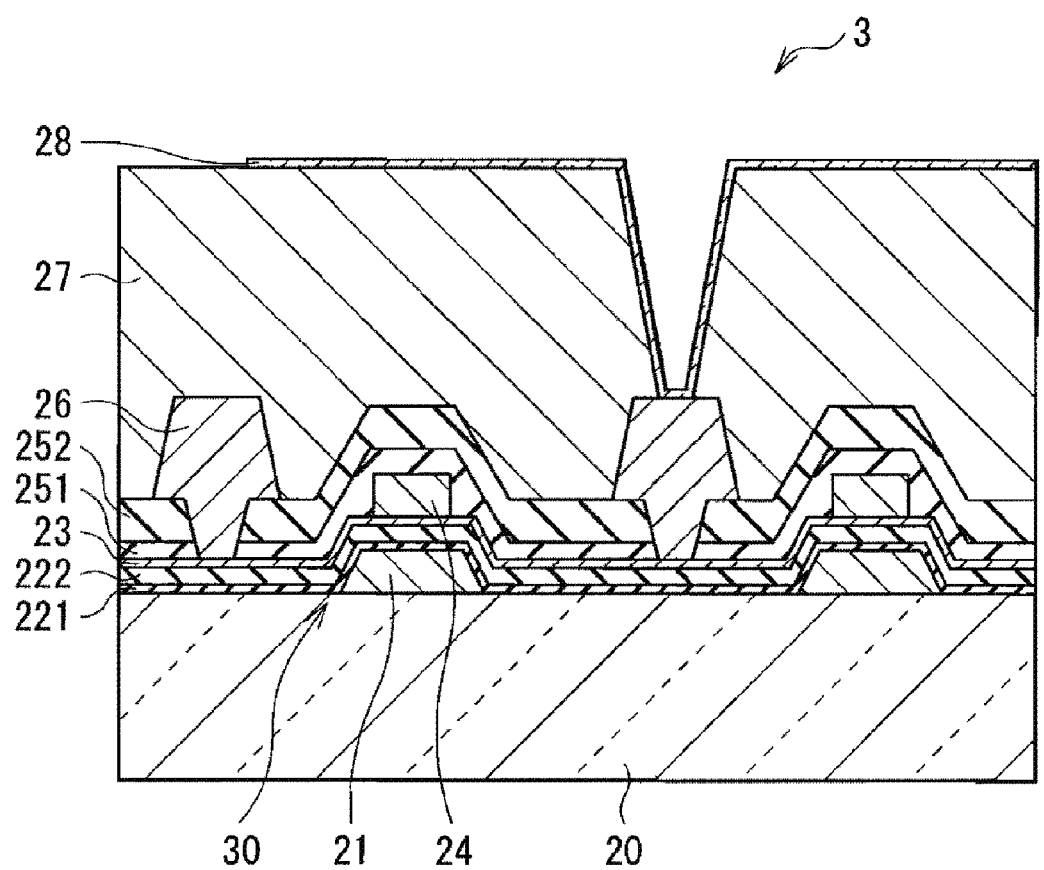
FIG. 13 is a cross sectional view illustrating an example of a structure of a TFT substrate including a semiconductor thin film formed by the steps of FIG. 2 to FIG. 5.

Further, for example, as illustrated in FIG. 13, the p-Si film 23 described in the foregoing embodiment is applicable to a TFT substrate 3 having a bottom gate type thin film transistor (TFT) used for manufacturing a liquid crystal display and an organic EL display. Specifically, in the Si thin film substrate 2 that has been provided with the inspection processing described in the foregoing embodiment, interlayer insulating films 251 and 252, a wiring 26, a planarizing film 27, and a transparent conductive film 28 are layered in this order over the p-Si film 23 by, for example, photolithography method. The interlayer insulating film 251 is composed of, for example, a silicon nitride (SiNx). The interlayer insulating film 252 is composed of, for example, silicon oxide ($SiO_2$). The wiring layer 26 is composed of, for example, aluminum (Al). The planarizing film 27 is composed of, for example, an acryl resin or the like. The transparent conductive film 28 is composed of, for example, an ITO (Indium Tin Oxide). Though FIG. 13 illustrates the TFT substrate having the bottom gate type TFT, the semiconductor thin film formed by the invention is also applicable to, for example, a TFT substrate having a top gate type TFT. Further, the semiconductor thin film formed by the invention is applied not only to the case for forming the TFT, but also to other semiconductor device.

Further, in the foregoing embodiment, the description has been given by taking the Si thin film (the a-Si film 230 and the p-Si film 23) as an example of amorphous semiconductor thin films and crystalline semiconductor thin films. However, the invention is applicable to a semiconductor thin film other than the Si thin film.

The present application contains subject matter related to that disclosed in Japanese Priority Patent Application JP 2007-211734 filed in the Japan Patent Office on Aug. 15, 2007, and Japanese Priority Patent Application JP 2008-208818 filed in the Japan Patent Office on Aug. 14, 2008 the entire content of which is hereby incorporated by references.

It should be understood by those skilled in the art that various modifications, combinations, sub combinations and alternations may occur depending on design requirements and other factors insofar as they are within the scope of the appended claims or the equivalents thereof.

What is claimed is:

1. A method of forming a semiconductor thin film comprising:
  a step of forming an amorphous semiconductor thin film over a transparent substrate;
  a step of forming a crystalline semiconductor thin film by irradiating the amorphous semiconductor thin film with laser light to provide heat treatment and thereby crystallizing the amorphous semiconductor thin film; and
  an inspection step of inspecting the crystalline semiconductor thin film,
  wherein,
    the inspection step includes a step of obtaining a transmission image of the crystalline semiconductor thin film by irradiating the crystalline semiconductor thin film with light from a rear side of the transparent substrate and taking an image, and a screening step of performing screening of the crystalline semiconductor thin film based on the obtained transmission image,
    in the screening step, a width of a crystallized region is obtained based on the obtained transmission image, and a crystallization state of the crystalline semiconductor thin film is inspected according to the width of the crystallized region, and
    in the step of obtaining the transmission image, an irradiated light in the green light wavelength range is generated by an LED light source for inspecting the crystalline semiconductor thin film.

2. The method of forming a semiconductor thin film according to claim 1, wherein:

the inspection step is a step of inspecting crystallinity of the crystalline semiconductor thin film, and further includes a step of generating a luminance distribution based on the obtained transmission image, and in the screening step, screening of the crystalline semiconductor thin film is performed by using the generated luminance distribution.

3. The method of forming a semiconductor thin film according to claim 2, wherein in the screening step, a standard deviation of luminance is calculated based on the luminance distribution, and screening of the crystalline semiconductor thin film is performed according to the standard deviation.

4. The method of forming a semiconductor thin film according to claim 3, wherein in the screening step, in the case where the standard deviation is under a given threshold value, determination is made so that the crystalline semiconductor thin film is a non-defective product, and in the case where the standard deviation is the given threshold value or more, determination is made so that the crystalline semiconductor thin film is a defective product.

5. The method of forming a semiconductor thin film according to claim 2, wherein in the screening step, a peak width of a luminance peak is calculated based on the luminance distribution, and screening of the crystalline semiconductor thin film is performed according to the peak width.

6. The method of forming a semiconductor thin film according to claim 5, wherein in the screening step, in the case where the peak width is larger than a given threshold value, determination is made so that the crystalline semiconductor thin film is a non-defective product, and in the case where the peak width is the given threshold value or less, determination is made so that the crystalline semiconductor thin film is a defective product.

7. The method of forming a semiconductor thin film according to claim 2, wherein in the screening step, a minimum value of luminance is calculated based on the luminance distribution, and screening of the crystalline semiconductor thin film is performed according to the minimum value.

8. The method of forming a semiconductor thin film according to claim 7, wherein in the screening step, in the case where the minimum value is larger than a given threshold value, determination is made so that the crystalline semiconductor thin film is a non-defective product, and in the case where the minimum value is the given threshold value or less, determination is made so that the crystalline semiconductor thin film is a defective product.

9. The method of forming a semiconductor thin film according to claim 1, wherein in the screening step, a distance between a previously set given reference pattern and a crystallized region and a direction thereof are respectively obtained based on the obtained transmission image, and a crystallization position of the crystalline semiconductor thin film is inspected based on the distance and the direction.

10. The method of forming a semiconductor thin film according to claim 1, wherein in the screening step, a spatial luminance distribution is obtained based on the obtained transmission image, and a physical destruction part in the crystalline semiconductor thin film is inspected based on the spatial luminance distribution.

11. The method of forming a semiconductor thin film according to claim 1, wherein in the step of forming the crystalline semiconductor thin film, irradiation with the laser light is performed by using a plurality of laser light sources, and thereby the heat treatment is provided.

12. The method of forming a semiconductor thin film according to claim 1, wherein in the step of forming the crystalline semiconductor thin film, irradiation with the laser light is performed by using a semiconductor laser light source.

13. The method of forming a semiconductor thin film according to claim 1, wherein the crystalline semiconductor thin film is used for forming a TFT (thin film transistor).

14. The method of forming a semiconductor thin film according to claim 1, wherein the crystalline semiconductor thin film is a Si (silicon) thin film.

* * * * *